(12) United States Patent
Khomenko et al.

(10) Patent No.: US 8,589,437 B1
(45) Date of Patent: Nov. 19, 2013

(54) DE-IDENTIFICATION AND SHARING OF GENETIC DATA

(75) Inventors: Oleksiy Khomenko, Stanford, CA (US); Alexander Wong, Palo Alto, CA (US); Anne Wojcicki, Palo Alto, CA (US); Linda Avey, Los Gatos, CA (US)

(73) Assignee: 23andMe, Inc., Mountain View, CA (US)

( * ) Notice: Subject to any disclaimer, the term of this patent is extended or adjusted under 35 U.S.C. 154(b) by 364 days.

(21) Appl. No.: 12/288,017

(22) Filed: Oct. 14, 2008

Related U.S. Application Data

(60) Provisional application No. 61/070,321, filed on Mar. 19, 2008, provisional application No. 60/999,148, filed on Oct. 15, 2007, provisional application No. 60/999,064, filed on Oct. 15, 2007.

(51) Int. Cl.
   *G06F 17/30* (2006.01)

(52) U.S. Cl.
   USPC .............................. 707/783; 707/770; 707/941

(58) Field of Classification Search
   USPC .................................................. 707/770, 781
   See application file for complete search history.

(56) References Cited

U.S. PATENT DOCUMENTS

| | | | |
|---|---|---|---|
| 5,974,409 A * | 10/1999 | Sanu et al. | 1/1 |
| 6,208,991 B1 * | 3/2001 | French et al. | 1/1 |
| 2004/0034550 A1 * | 2/2004 | Menschik et al. | 705/3 |
| 2005/0010435 A1 * | 1/2005 | Kato et al. | 705/2 |
| 2005/0108551 A1 * | 5/2005 | Toomey | 713/185 |
| 2008/0131887 A1 * | 6/2008 | Stephan et al. | 435/6 |
| 2008/0222299 A1 * | 9/2008 | Boodaei | 709/229 |
| 2009/0132282 A1 * | 5/2009 | Kerstna et al. | 705/3 |

* cited by examiner

*Primary Examiner* — Sangwoo Ahn
(74) *Attorney, Agent, or Firm* — Van Pelt, Yi & James LLP

(57) ABSTRACT

A system for separating identifying data from personal data is disclosed. The system includes: a first set of stored data comprising a plurality of identifying data structures containing identifying data; a second set of stored data comprising a plurality of personal data structures containing personal data; a set of mapping data comprising a plurality of mappings, wherein each mapping is between an identifying data structure and a personal data structure; and an application configured to receive mapping data associated with a mapping, determine a mapping associated with the mapping data, and obtain a personal data structure based on the mapping. The set of mapping data is logically separate from the first set of stored data, the second set of stored data, and the application.

29 Claims, 25 Drawing Sheets my health and traits
Age-related Macular Degeneration

Your Genetic Data

Show information for [Alex Wong ▼] assuming [European ▼] ethnicity and an age range of [40-79 ▼]
- Alex Wong
- Greg Mendel (Dad)
- Lilly Mendel (Mom)

Where's mine?

Alex Wong
4.8 out of 100 people of European ethnicity who share Alex Wong's genotype will get Age-related Macular Degeneration between the ages of 40 and 79.

4.8

Average
7.7 out of 100 people of European ethnicity will get Age-related Macular Degeneration between the ages of 40 and 79.

7.7

What does the Odds Calculator show me?

Use the ethnicity and age range selectors above to see the estimated incidence of Age-related Macular Degeneration due to genetics for someone with Alex Wong's genotype. The 23andMe Odds Calculator assumes that a person is free of the condition at the lower age in the range. You can use the name selector above to see the estimated incidence of Age-related Macular Degeneration for the genotypes of other people in your account.

The 23andMe Odds Calculator only takes into account effects of markers with known associations that are also on our genotyping chip. Keep in mind that aside from genetics, environment and lifestyle may also contribute to one's chances of developing late-stage AMD.

NOTE: Click here to read about recent changes to the Odds Calculator.

Alex Wong | help | log out

FIG. 1B

Alex Wong | help | log out my health and traits
Alcohol Flush Reaction

Your Genetic Data

| Who | Genotype | What It Means | Genes vs. Environment |
|---|---|---|---|
| Alex Wong | AA | No working copies of ALDH2. Extreme flushing reaction to alcohol. Highly unlikely to become dependent on alcohol. | Sensitivity to alcohol– the alcohol flush reaction– depends almost entirely on a person's genotype at two genes, ALDH2 and ADH1B. 23andMe currently reports your genotype at a SNP in ALDH2.It is possible that those with the AG or GG genotypes at the SNP are more sensitive to alcohol due to their genotype at ADH1B (which 23andMe does not report). |
| | AG | One working copy of ALDH2 Moderate flushing reaction to alcohol. Somewhat less likely than average to become dependent on alcohol. | |
| Greg Mendel (Dad), Lilly Mendel (Mom) | GG | Two working copies of ALDH2 Little or no flushing reaction to alcohol. | |

FIG. 1C close or Esc Key

Invite People to Share Genomes

To share with friends or family, ask or search for their 23andMe usernames and enter them below. What will I be sharing?

| | |
|---|---|
| Username: | [_____] ─502 |
| | *To invite multiple people at once, add commas between usernames.* |
| Profiles: | ☑ Ian Mendel |
| Level: | ⦿ Basic  ○ Complete |
| Message text: | Let's share our profiles on 23andMe and compare our genomes. |
| | *Maximum message length is 500 characters.* |

[ invite ]

FIG. 5

Account Records 1101

| ACCOUNT ID | ACCOUNT USERNAME | PASSWORD | ACCOUNT NAME | ACCOUNT EMAIL ADDRESS | SHIPPING ADDRESS |
|---|---|---|---|---|---|
| 50001 | familydoe | password_x | The Doe Family | john@doe.com | 5 Market St., San Francisco, CA 94132 |
| 50002 | boblee | password_y | Bob Lee | bob@lee.com | P.O. Box 8, New York, NY 10027 |
| ... | | | | | ... |

Profile Records 1102

| PROFILE ID | ACCOUNT ID | PROFILE NAME | PROFILE EMAIL ADDRESS | BIRTHDATE | BIRTHPLACE | CURRENT LOCATION | ANCESTRY |
|---|---|---|---|---|---|---|---|
| 10001 | 50001 | John Doe | john@doe.com | 11/15/1975 | San Francisco | San Francisco | European |
| 10002 | 50001 | Mary Doe | mary@doe.com | 9/7/1977 | Los Angeles | San Francisco | European |
| 10003 | 50002 | Bob Lee | bob@lee.com | 2/4/1968 | New York | New York | Asian |
| ... | | | | | | | ... |

FIG. 11A

Phenotype Records 1104

| PHENOTYPE ID | HEIGHT | WEIGHT | EYE COLOR | HAIR COLOR | ... |
|---|---|---|---|---|---|
| 20001 | 5'5" | 120 lb | Blue | | |
| 20002 | | | | | |
| 20003 | 5'10" | 170 lb | Brown | Brown | |
| 20004 | | | | | |
| 20005 | | | | | |
| ... | | | | | ... |

Genotype Records 1106

| GENOTYPE ID | SNP DATA | TEST RESULT 1 | TEST RESULT 2 | ... |
|---|---|---|---|---|
| 30001 | | Yes | | |
| 30002 | | No | | |
| 30003 | SNP_x | No | 0.8 | |
| 30004 | SNP_y | Yes | 0.14 | |
| ... | | | | ... |

FIG. 11B

Sharing Table 1200

| ACCOUNT SHARED TO | PROFILE SHARED FROM | SHARING LEVEL |
|---|---|---|
| 50002 | 10001 | Basic |
| 50002 | 10002 | Extended |
| ... | ... | ... |
| | | |

FIG. 12

Mapping Records 1500

| PROFILE ID | GENOTYPE ID | PHENOTYPE ID |
|---|---|---|
| 10001 | 30004 | 20003 |
| 10002 | 30003 | 20001 |
| 10003 | 30001 | 20005 |
| . . . | . . . | . . . |

FIG. 15

Mappings for boblee 1700

| PROFILE ID | GENOTYPE ID | PHENOTYPE ID |
|---|---|---|
| 10003 | 30001 | 20005 |
| 10001 | 30004 | 20003 |
| 10002 | 30003 | 20001 |
| ... | ... | ... |

FIG. 17

Token Cache 1800

| Session Token | Mappings | Sharing Level |
|---|---|---|
| Token_x | 10003 20005 30001 | |
| | 10001 30004 20003 | Basic |
| | 10002 30003 20001 | Extended |
| ... | ... | ... |
| | | |
| | | |

FIG. 18

Profile Records 1900

| PROFILE ID | ACCOUNT ID | PROFILE NAME | PROFILE EMAIL ADDRESS | BIRTHDATE | BIRTHPLACE | CURRENT LOCATION | ANCESTRY | PUBLIC DATA | GROUP DATA |
|---|---|---|---|---|---|---|---|---|---|
| 10001 | 50001 | John Doe | john@doe.com | 11/15/1975 | San Francisco | San Francisco | European | TestResult1=Yes; Height=5'10" | GroupID=6002; Weight=170 lb |
| 10002 | 50001 | Mary Doe | mary@doe.com | 9/7/1977 | Los Angeles | San Francisco | European | | |
| 10003 | 50002 | Bob Lee | bob@lee.com | 2/4/1968 | New York | New York | Asian | | |
| ... | | | | | | | ... | | |

FIG. 19

DE-IDENTIFICATION AND SHARING OF GENETIC DATA

CROSS REFERENCE TO OTHER APPLICATIONS

This application claims priority to U.S. Provisional Patent Application No. 61/070,321 entitled GENOME SHARING filed Mar. 19, 2008 and to U.S. Provisional Patent Application No. 60/999,148 entitled GENETIC INFORMATION SITE filed Oct. 15, 2007 and to U.S. Provisional Patent Application No. 60/999,064 entitled GENOME EXPLORER filed Oct. 15, 2007.

BACKGROUND OF THE INVENTION

Recently, interest in genetics and genetic testing has risen as increasing amounts of research show how an individual's genetic information can influence aspects of a person's ancestry, appearance, behavior, and physiology. Genetic information can be made available to an individual via the Internet. To prevent others from viewing personal data, the individual is typically required to login using a password in order to gain access to his data. In some cases, an individual may wish to share his personal data with one or more other individuals, such as family members. However, current techniques for sharing personal data are basic and have limited capability. In addition, current techniques may be vulnerable to attack, potentially allowing personal data to be compromised. As such, improvements in the sharing of personal data would be useful.

BRIEF SUMMARY OF THE INVENTION

A system for separating identifying data from personal data is disclosed. In some cases, if an unauthorized user obtains access to the identifying data and the personal data, the unauthorized user would not be able to determine which identifying data is associated with which personal data without access to secured mapping data.

The system includes: a first set of stored data stored in a computer data storage comprising a plurality of identifying data structures containing identifying data, a second set of stored data stored in a computer data storage comprising a plurality of personal data structures containing personal data, a set of mapping data stored in a computer data storage comprising a plurality of mappings, wherein each mapping is between an identifying data structure and a personal data structure, and an application configured to receive mapping data associated with a mapping, determine a mapping associated with the mapping data, and obtain a personal data structure based on the mapping. The set of mapping data is in a logically separate database from the first set of stored data, the second set of stored data, and the application. The personal data structures do not contain identifying data used to identify an individual. In the event that an unauthorized user obtains access to the first set of stored data and the second set of stored data, the unauthorized user would not be able to determine which personal record is associated with each identifying record without access to the mapping data.

BRIEF DESCRIPTION OF THE DRAWINGS

Various embodiments of the invention are disclosed in the following detailed description and the accompanying drawings.

FIGS. 1B-1D illustrate examples embodiments of interfaces for displaying genetic data from multiple users.

FIG. 5 is a diagram illustrating an example of an interface for a sharing invitation.

FIGS. 11A-11B are diagrams illustrating an embodiment of records in various databases in a system for sharing genetic or other data.

FIG. 12 is a diagram illustrating an embodiment of a sharing table.

FIG. 15 is a diagram illustrating an embodiment of mapping records in a mapping database.

FIG. 17 is a diagram illustrating a set of mappings for boblee.

FIG. 18 is a diagram illustrating an embodiment of a token cache.

FIG. 19 is a diagram illustrating an embodiment of profile records in a system with publishing and group sharing features.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1A:
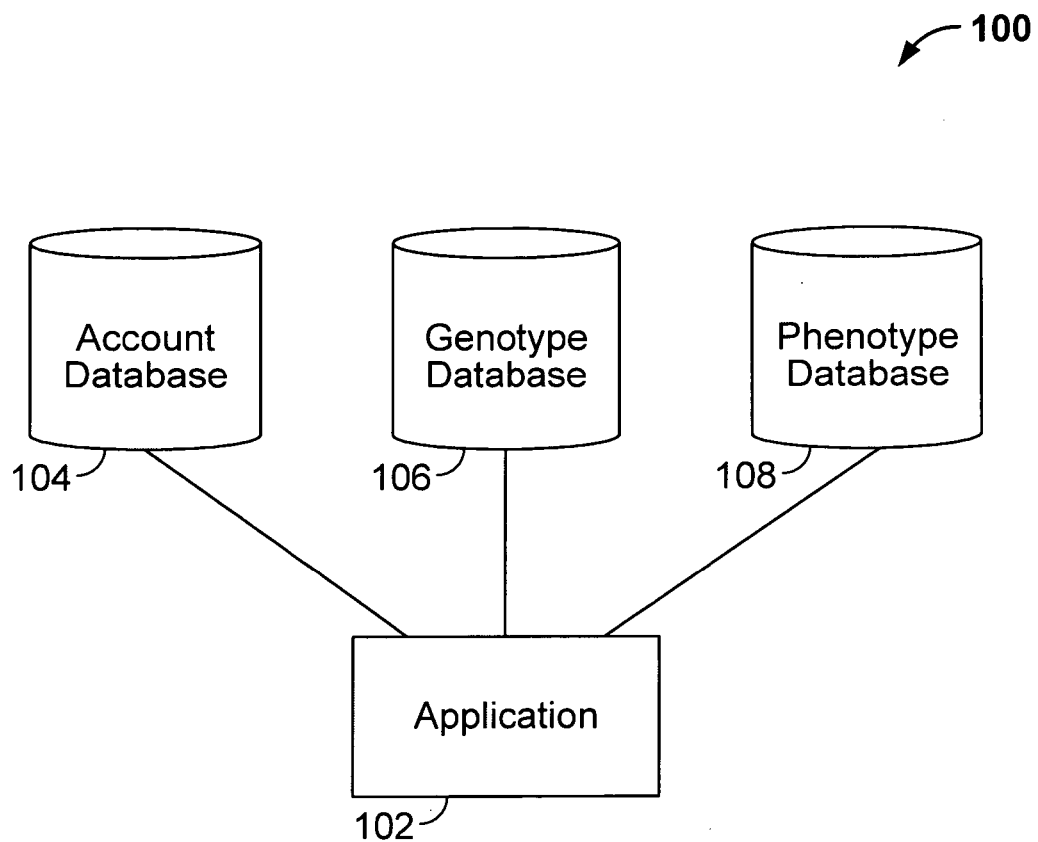
FIG. 1A is a block diagram illustrating an embodiment of a system for sharing genetic or other data.

FIG. 1A is a block diagram illustrating an embodiment of a system for sharing genetic or other data. In the example shown, system 100 is shown to include application 102, account database 104, genotype database 106 and phenotype database 108. Application 102 interacts with account database 104, genotype database 106 and phenotype database 108 to access data associated with an individual. Account database 104 contains identifying data associated with individuals, such as names, addresses, etc. Genotype database 106 contains data associated with the individuals' genetics, such as single nucleotide polymorphism (SNP) data, including calls for various SNPs or genetic test results. Phenotype database 108 includes data associated with the individuals' phenotypes, such as hair color, eye color, birth date, or medical conditions. Phenotype data can be obtained based on user survey(s) or other interactive tools. A phenotype includes any observable characteristic of an organism, such as its morphology, development, biochemical or physiological properties, or behavior. Phenotypes are influenced by a combination of genetic and environmental factors.

In some embodiments, application 102 is a web application that is part of a website that allows individuals to view their genetic and other personal data. An example of such a website is www.23andme.com. An individual may use such a website to ascertain descriptions of certain traits they have and the genes associated with them. For example, the website www.23andme.com provides an odds calculator that can combine genetic and phenotypic information, age, and ethnicity to get an idea of which common health concerns are most likely to affect the individual. Such an odds calculator may be used by an individual to determine information for an individual such as his likelihood of developing type 2 diabetes. Additionally, such a website may allow an individual to determine if they have a particular gene, such as the one that allows for tasting the bitter flavor of broccoli.

Figure 1D:

In some embodiments, application 102 allows an individual to share at least a subset of his genetic and other personal data with other users. FIGS. 1B-1D illustrate examples embodiments of interfaces for displaying genetic data from multiple users. For example, in FIGS. 1B-1C, a user may view descriptions of traits or odds associated with different health concerns associated with other individuals. In another example, FIG. 1D, a "Genome Browser" interface allows a user to view his raw genome data and the raw genome data of other individuals with which sharing of raw genome data has been established. In some embodiments, the raw genome data for multiple individuals are displayed together.

Although databases, records, fields, rows, and columns may be described herein, in various embodiments, any appropriate technique for storing data may be used. A database is an example of a set of stored data. In various embodiments, any appropriate set of stored data may be used besides a database. A set of stored data may include a data repository or data store, such as a database or a file. A set of stored data may include one or more data structures, such as records, rows, or objects.

Figure 2:
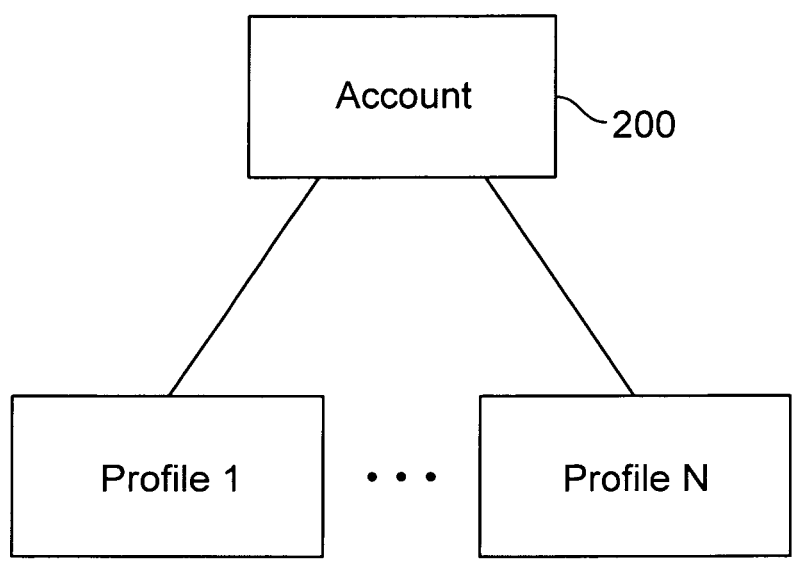
FIG. 2 is a block diagram illustrating an embodiment of an account in a web application that allows sharing of personal data.

FIG. 2 is a block diagram illustrating an embodiment of an account in a web application that allows sharing of personal data. In some embodiments, account 200 is stored in account database 104. In the example shown, an individual (e.g., John Doe) signs up for an account 200 in the web application by specifying a username, password, security question, and birth date. In some embodiments, terms of service (TOS) are displayed and a user must agree to the TOS in order to sign up for an account. In order to access the account in the web application, the username and password must be specified. An account can own 0 or more profiles. Each profile is associated with a different individual or human being. For example, profiles 1-3 might be for John Doe, Mary Doe (his wife), and Bobby Doe (his son), respectively. In the example shown, N profiles are owned by account 200. Stated another way, account 200 owns N profiles. In some embodiments, anyone with access to account 200 has read and/or write access to (i.e., is able to or has permission to view and/or modify) any of profiles 1-N. In some embodiments, profiles 1-N each contain data associated with an individual, such as name and birthdate, and account 200 contains data that is not specific to an individual, such as an account name (e.g., The Doe Family), an account username (e.g., doefamily) and password.

In some embodiments, a profile may be transferred from one account to another. For example, Mary Doe divorces John Doe and would like to set up her own account to own her profile. As another example, Bobby Doe grows up (e.g., turns 18) and would like to have his profile owned by his own account. In some embodiments, a profile can only be owned by one account, so once Mary Doe's profile is owned by Mary Doe's account, then it is no longer owned by John Doe's account. In some embodiments, a user logs into the doefamily account to request the transfer and a user logs into Mary Doe's account to accept the transfer. In some embodiments, when the user of the doefamily account requests the transfer, the user must provide a password associated with the destination account and/or answer a secret question.

Figure 3:
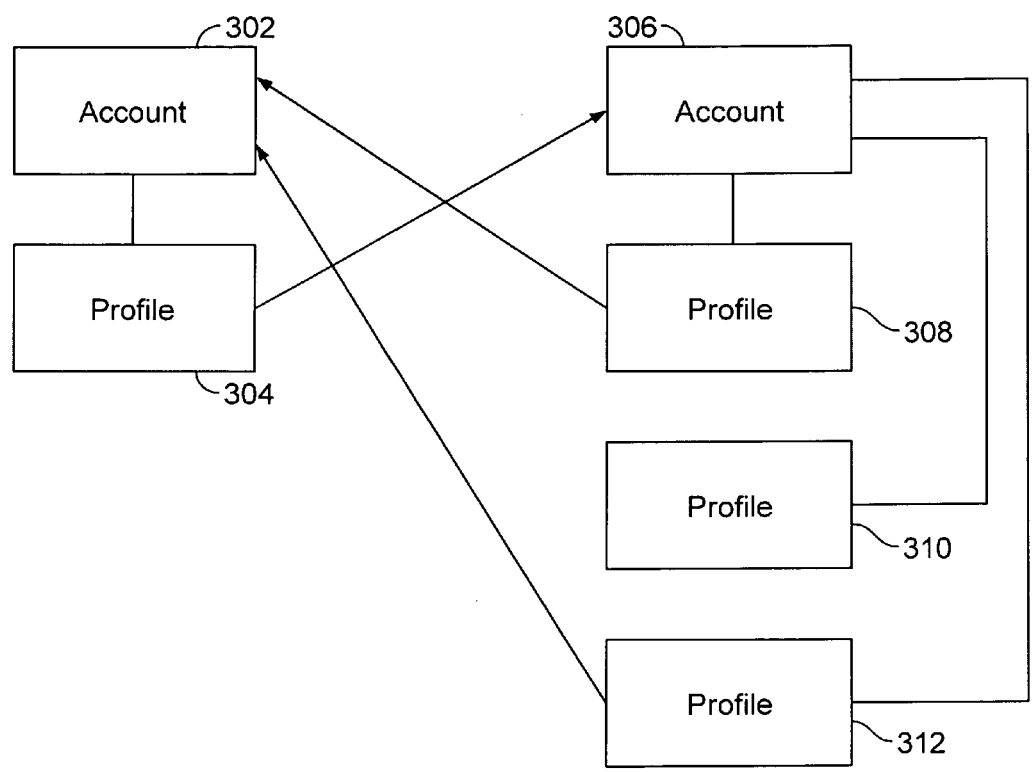
FIG. 3 is a block diagram illustrating an embodiment of sharing of personal data.

FIG. 3 is a block diagram illustrating an embodiment of sharing of personal data. In the example shown, account 302 owns profile 304 and account 306 owns profiles 308, 310, and 312. Profiles 308 and 312 are shared with or "shared to" account 302. Stated another way, sharing has been established from profiles 308 and 312 to account 302. In other words, account 302 has read access to (e.g., is able to or has permission to view) at least a subset of data associated with profiles 308 and 312.

Profile 304 is shared with or "shared to" account 306. Stated another way, sharing has been established from profile 304 to account 306. In other words, account 306 has read access to at least a subset of data associated with profile 304. In some embodiments, certain data associated with a profile is public data; that is, any other account has read access to public data. In such embodiments, when a profile is shared to an account, it means that the account has read access to at least a subset of nonpublic data associated with the profile.

Figure 4:
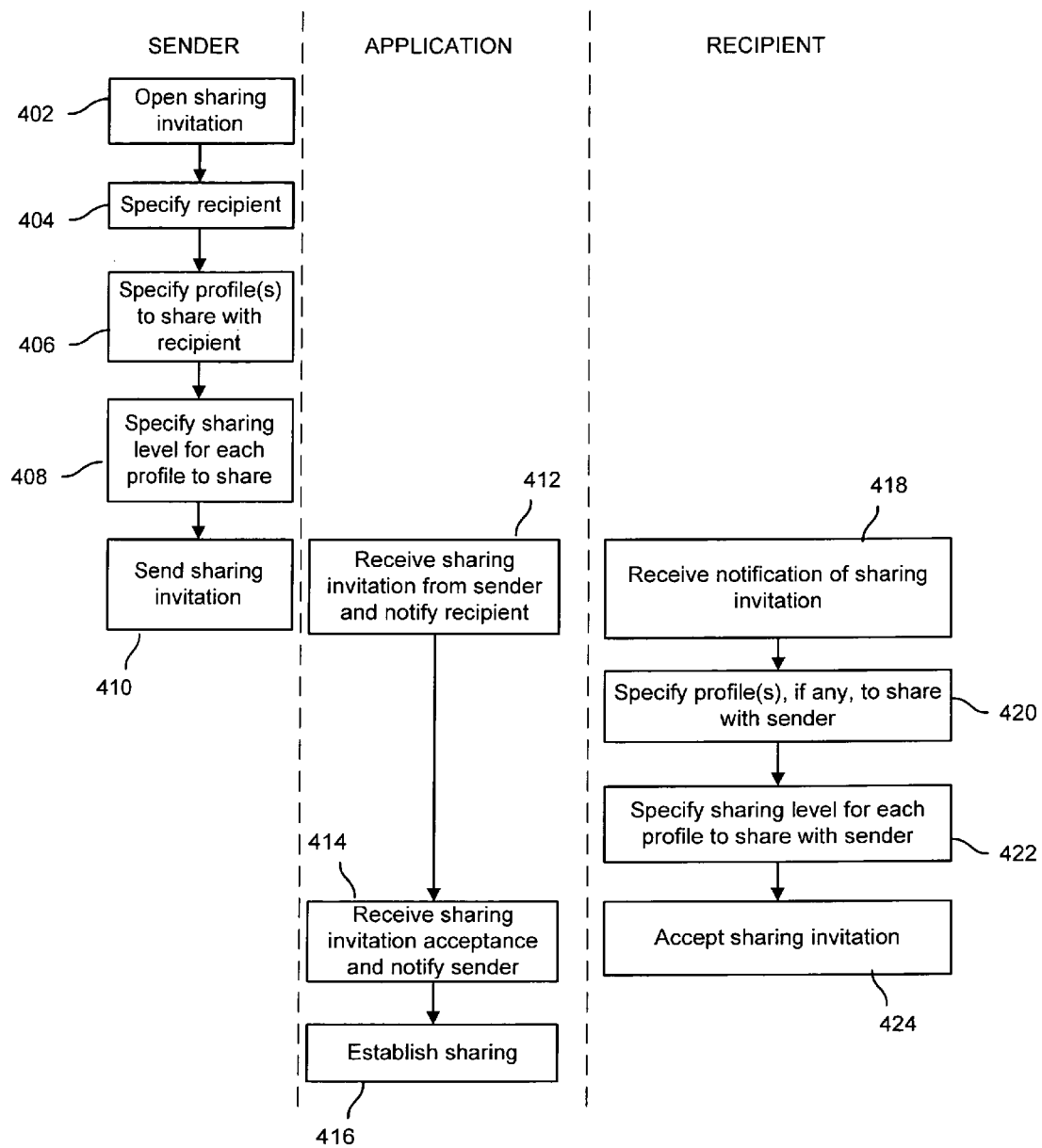
FIG. 4 is a flow chart illustrating an embodiment of a process for initiating and establishing sharing.

FIG. 4 is a flow chart illustrating an embodiment of a process for initiating and establishing sharing. In some embodiments, process 400 or at least steps 412-416 are performed by application 102. In some embodiments, steps 402-410 are associated with a first account. For example, a user of the first account causes steps 402-410 to be performed. In some embodiments, steps 418-424 are associated with a second account. For example, a user of the second account causes steps 418-424 to be performed.

In the example shown, at 402, a sharing invitation is opened. For example, a user logs into a first account and then opens an interface for a sharing invitation. FIG. 5 is a diagram illustrating an example of an interface for a sharing invitation.

At 404, a recipient is specified. For example, the interface may provide a place to enter a recipient. In FIG. 5, the user can enter or search for usernames using box 502. In some embodiments, an account user can specify that the account username (e.g., doefamily) and/or account name (e.g., The Doe Family) is searchable. In some embodiments, names and/or email addresses associated with profiles (e.g., John Doe, Mary Doe, and/or Bobby Doe) may be searchable. In some embodiments, the user can search based on other information, such as Current Location, type 1 diabetes risk, etc. In some embodiments, in order for data to be searchable, the data must be made public.

In some embodiments, 404 is performed before 402. For example, a user's profile may be publicly represented on the website. For example, if a user has posted a message in a community thread, his or her profile picture and public nickname will be displayed in that thread. Another user may click on the picture or nickname to view the posting user's profile page. From this page, the other user may initiate a sharing invitation by clicking on an invitation link. In this case, the inviting user does not need to specify the invitee again in the invitation, as it is inherited from the profile page on which the invitation link was clicked. An invitation link may also be found next to the posting user's picture and nickname, in which case the inviting user can click directly on that link to invite without first going to the invitee's profile page.

Alternatively, a user's profile may be found and an invitation sent to them through user search results.

At 406, profile(s) to share with the recipient are specified. For example, the profiles for John Doe and Mary Doe may be specified. Then the profile for Bobby Doe will not be shared. In FIG. 5, the profile Ian Mendel is the only profile associated with the account and it is selected as the profile to share. In some embodiments, if there is only one profile associated with the account, this step is skipped and the one profile is selected by default. In some embodiments, the sender can select no profiles to share with the recipient.

At 408, a sharing level for each profile to share is specified. A sharing level indicates a subset of data associated with the profile to share or to which to provide read access. A sharing level may be embodied in various ways. Specific data to share may be individually indicated, or groups of data to be shared may be indicated. In FIG. 5, two sharing levels may be indicated: "Basic" or "Complete". When "Basic" is selected, then a smaller subset of data is shared than when "Complete" is selected. For example, "Basic" might include ancestry and general comparison features, while "Complete" might include detailed health and traits articles and odds calculations, or full SNP-level information in the form of a genome browser. In some embodiments, a sharing level to request from the other account holder is also specified. The user may also request certain profiles from other account. In some embodiments, the sharing level is implicitly symmetric, so that the sharing level from the sender to the recipient is the same as the sharing level from the recipient to the sender. The sender may also attach a personal message to the invitation.

At 410, the sharing invitation is sent. For example, in FIG. 5, the "invite" button is selected. In some embodiments, the sharing invitation includes the sharing levels specified at 408.

At 412, the sharing invitation is received from the sender and the recipient is notified. For example, the web application is notified that the sharing invitation was sent and sends an email to the recipient.

At 418, a notification of the sharing invitation is received. For example, the recipient receives an email message notifying him that a sharing invitation has been received and to login to his account to respond to it.

Figure 6:
FIG. 6 is a diagram illustrating an example of an interface for responding to a sharing invitation.

At 420, profile(s) to share with the sender, if any, are specified. For example, the recipient logs into his account and an interface is presented for responding to the invitation. FIG. 6 is a diagram illustrating an example of an interface for responding to a sharing invitation. In this example, Alex Wong is the sender of the invitation and has requested sharing level Basic. The recipient can select one or more profiles to share back with the sender. In some embodiments, the recipient can select no profiles to share back with the sender. In some embodiments, if there is only one profile associated with the account, this step is skipped and the one profile is selected by default.

At 422, a sharing level for each profile to share back with the sender is specified. In some embodiments, the recipient can specify a sharing level (e.g., Basic or Complete) for each profile to be shared back. (In FIG. 6, this option is not available.)

At 424, the sharing invitation is accepted. For example, in FIG. 6, the "OK" button is selected.

At 414, the sharing invitation acceptance is received from the recipient and the sender is notified. For example, the web application is notified that the sharing invitation was accepted and sends an email to the recipient.

At 416, sharing is established. In some embodiments, before sharing can be established, the sender reconfirms the request by logging into the sender's account and reconfirming the request. In some cases, the sender may decide not to reconfirm the request, if, for example, at 420, the sender does not recognize the recipient, who may be a hacker.

In some embodiments, each account only has one profile, so steps 406 and 420 are skipped. In some embodiments, sharing levels are preset and steps 408 and 422 are skipped. In some embodiments, the sharing levels are bidirectional (the same in both directions) so that whatever sharing level is specified at 408 is automatically the sharing level specified at 422. Thus, step 422 may be skipped and the sharing level preset to the sharing level specified at 408.

Once sharing is established, sharing levels may change, sharing may be terminated, etc. In some embodiments, sharing is unilaterally stopped. In other words, when the sharing of a first account's profile to a second account is terminated, then sharing from the second account's profile to the first account is automatically terminated. In some embodiments, either party can terminate sharing. In some embodiments, one or more levels of sharing may be upgraded and/or downgraded.

Figure 7:
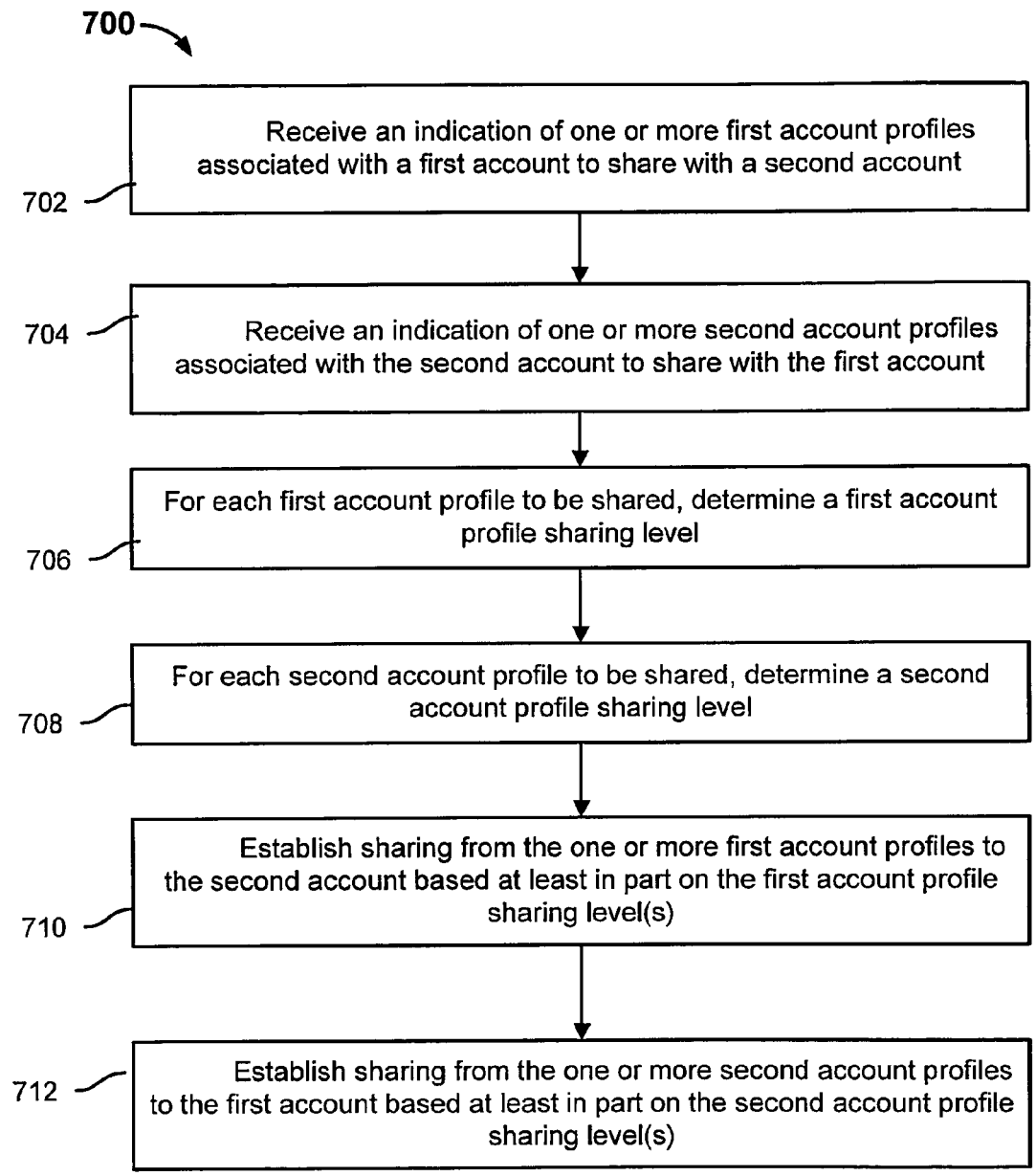
FIG. 7 is a flow chart illustrating an embodiment of a process for establishing sharing.

FIG. 7 is a flow chart illustrating an embodiment of a process for establishing sharing. In some embodiments, process 700 is used to perform steps 412-416. In the example shown, at 702, an indication of one or more first account profiles associated with a first account to share with a second account is received. For example, if a user is providing information as in FIG. 4, the profile(s) specified at 406 are received. At 704, an indication of one or more second account profiles associated with the second account to share with the first account is received. For example, the profile(s) specified at 420 are received. At 706, for each first account profile to be shared, a first account sharing level is determined. For example, the sharing level(s) specified at 408 are determined. At 708, for each second account profile to be shared, a second account sharing level is determined. For example, the sharing level(s) specified at 422 are determined. At 710, sharing is established from the one or more first account profiles to the second account based at least in part on the first account profile sharing level(s). At 712, sharing from the one or more second account profiles to the first account is established based at least in part on the second account profile sharing level(s). In some embodiments, steps 702-708 result from what a user specifies in a web interface to a web application.

Figure 8:
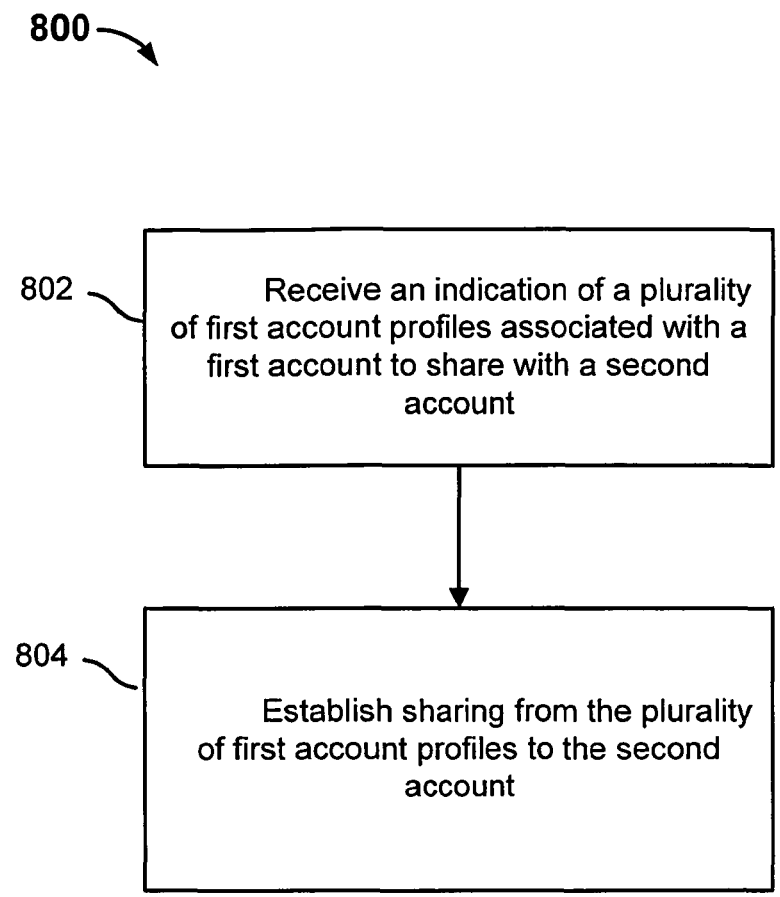
FIG. 8 is a flow chart illustrating an embodiment of a process for establishing sharing of multiple profiles.

FIG. 8 is a flow chart illustrating an embodiment of a process for establishing sharing of multiple profiles. In some embodiments, process 800 is used to perform steps 412-416. In the example shown, at 802, an indication of a plurality of first account profiles associated with a first account to share with a second account is received. At 804, sharing from the plurality of first account profiles to the second account is established. Sharing comprises the second account having read access to a subset of nonpublic data associated with the plurality of first account profiles.

Figure 9:
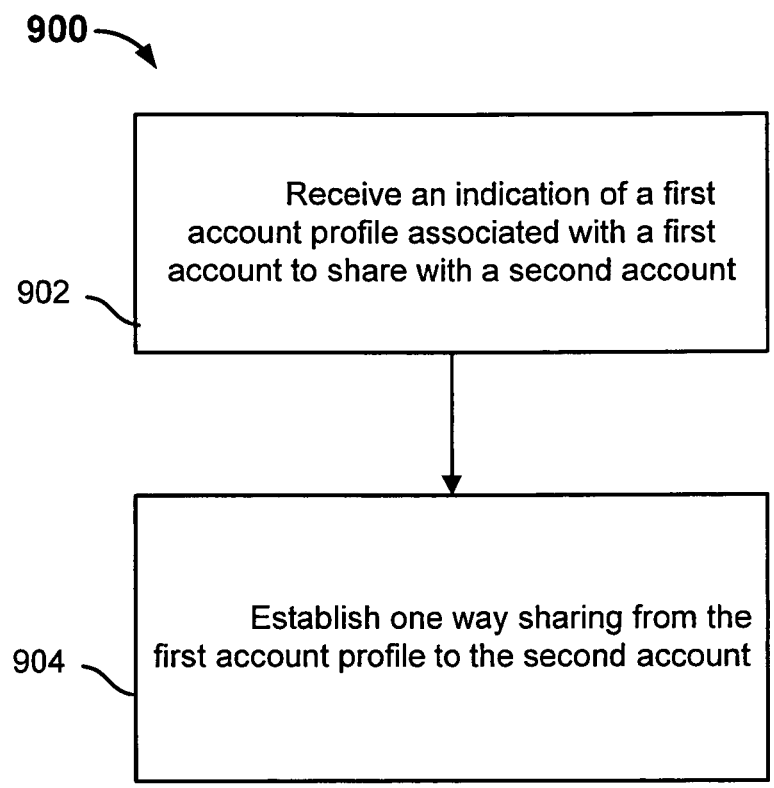
FIG. 9 is a flow chart illustrating an embodiment of a process of establishing one way or unidirectional sharing.

FIG. 9 is a flow chart illustrating an embodiment of a process of establishing one way or unidirectional sharing. In some embodiments, process 900 is used to perform steps 412-416. In the example shown, at 902, an indication of a first account profile associated with a first account to share with a second account is received. At 904, one way sharing from the first account profile to the second account is established. One way sharing means that the second account has read access to a subset of nonpublic data associated with the first account profile, but the first account does not have read access to nonpublic data associated with the first account. For example, an individual may share the individual's data with a doctor, but the doctor does not need to share the doctor's data back to the individual.

Figure 10:
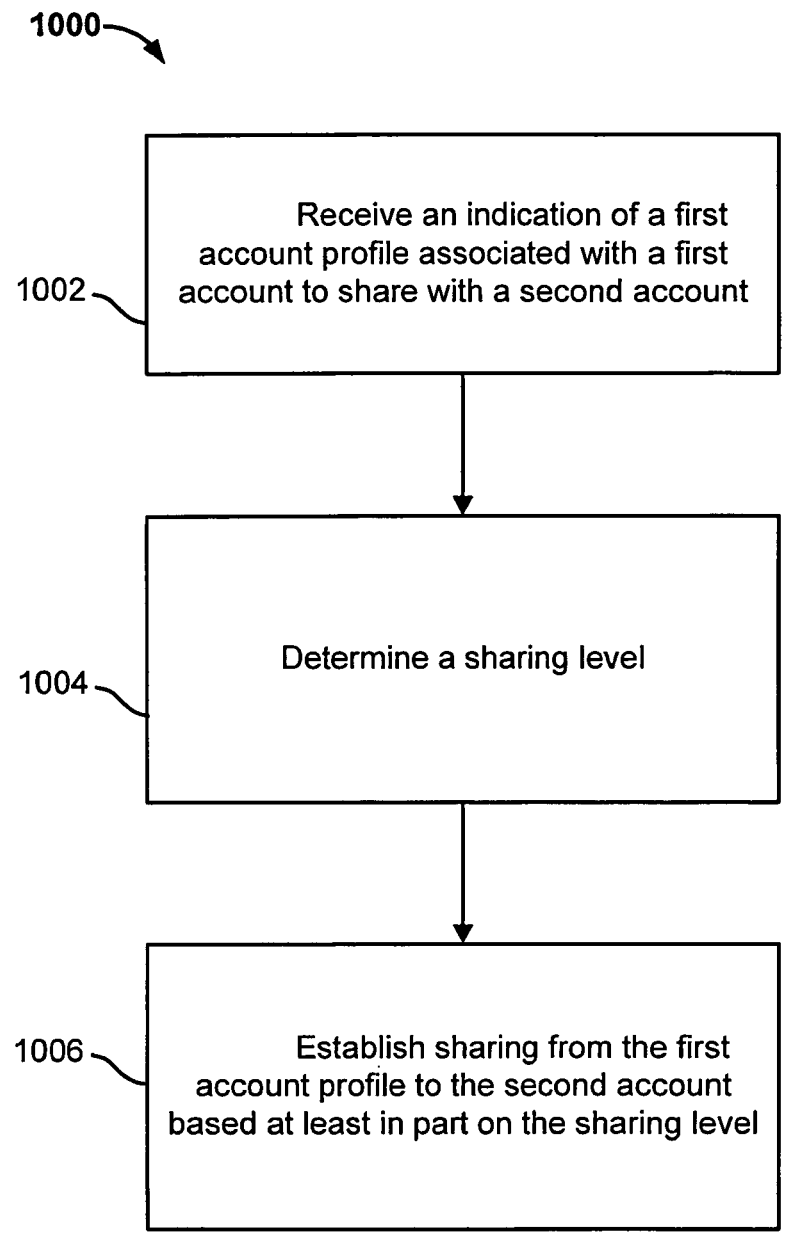
FIG. 10 is a flow chart illustrating an embodiment of a process for establishing sharing using sharing level(s).

FIG. 10 is a flow chart illustrating an embodiment of a process for establishing sharing using sharing level(s). In some embodiments, process 1000 is used to perform step 416. In the example shown, at 1002, an indication of a first account profile associated with a first account to share with a second account is received. At 1004, a sharing level is determined. In some embodiments, the sharing level indicates a subset of data associated with the first account profile to share with the second account. At 1006, sharing from the first account profile to the second account is established based at least in part on the sharing level. In some embodiments, sharing comprises the second account having read access to the subset of data indicated by the sharing level.

FIGS. 11A-11B are diagrams illustrating an embodiment of records in various databases in a system for sharing genetic or other data. In the example shown, account records 1101 and profile records 1102 are stored in an account database, such as account database 104. Phenotype records 1104 are stored in a phenotype database, such as phenotype database 108. Genotype records 1106 are stored in a genotype database, such as genotype database 108.

Referring to FIG. 2, in some embodiments, each account record 1101 is an example of account 200 and each profile record 1102 is an example of one of profiles 1-N.

In the example shown, each account record includes: "Account ID", "Account Username", "Password", "Account Name", "Account Email Address", and "Shipping Address". In some embodiments, "Account ID" uniquely identifies each account record. In some embodiments, the "Password" is encrypted using a hash function.

In some embodiments, profile records 1102 include data that can be used to identify an individual. In some embodiments, each profile record 1102 is associated with a different individual. An individual can be a person or in some embodiments, an animal, such as a pet. Each profile record includes: "Profile ID", "Account ID", "Profile Name", "Profile Email Address", "Birthdate", "Birthplace", "Current Location", and "Ancestry". In some embodiments, "Profile ID" uniquely identifies each profile record.

An account may own or be associated with one or more profile records. In profile records 1102, "Account ID" indicates the account that owns or is associated with each profile record. As shown, multiple profile records may have the same "Account ID" or be associated with the same account. When a profile is transferred from one account to another account, the "Account ID" of the profile is updated to the new account's "Account ID".

In some embodiments, account records contain data that is not specific to an individual. In some embodiments, profile records contain data associated with an individual. In some embodiments, each account record also includes a "Profiles" field. "Profiles" includes the Profile IDs of the profile records associated with the account.

Referring to FIG. 11B, in the example shown, each phenotype record includes: "Phenotype ID", "Height", "Weight", "Eye Color", and "Hair Color". Other examples of fields that may be included in a phenotype record include medical conditions, such as whether the individual has type 1 diabetes, survey answers, or data collected from interactive tools. In some embodiments, phenotype records 1104 include data associated with the phenotype of an individual. In some embodiments, "Phenotype ID" uniquely identifies each phenotype record.

In the example shown, each genotype record includes: "Genotype ID", "SNP Data", "Test Result 1", and "Test Result 2". In some embodiments, "SNP Data" includes calls for various SNPs and confidence values for the calls for the individual. "Test Result 1" and "Test Result 2" could be results of a genetic test, such as whether the individual can taste bitterness in broccoli, or the individual's type 1 diabetes risk. In some embodiments, "Genotype ID" uniquely identifies each genotype record.

In some embodiments, an application such as application 102 retrieves profile records, phenotype records, and genotype records as needed in order to provide genetic or other data to users over the Internet.

In some embodiments, some of the fields shown in profile records 1102 are stored in separate records in a separate database. For example, the "Birthdate", "Birthplace", and "Ancestry" fields could be stored in biographical records in a biographical database. The biographical records might also include a social security number. This way, should a hacker obtain access to the profile records, he could not determine which profile records belong to which biographical records. This may be useful to address concerns of identity theft.

FIG. 12 is a diagram illustrating an embodiment of a sharing table. In some embodiments, a sharing table is used to store sharing information from the various profiles to the various accounts in system 100. In the example shown, sharing table 1200 includes three columns: "Account Shared To", "Profile Shared From", and "Sharing Level". The first row of sharing table 1200 indicates that the profile 10001 is shared to the account 50002 at a basic sharing level. As shown in FIG.

11A, profile 10001 is associated with account 50001 having username familydoe. Account 50002 is associated with username boblee. Thus, a user of account 50001 has allowed users of account 50002 read access to a subset of nonpublic data in profile 10001. The subset is specified by the sharing level, in this case Basic. In some embodiments, the Basic sharing level means there is read access to a basic subset of nonpublic data and the Extended sharing level means there is read access to an extended subset of nonpublic data, wherein the extended subset is a superset of the basic subset.

In some embodiments, there are three or more sharing levels available. In some embodiments, the level of sharing can be individually configured at a lower level of granularity. For example, a user may specifically select which data to which to allow read access.

Figure 13:
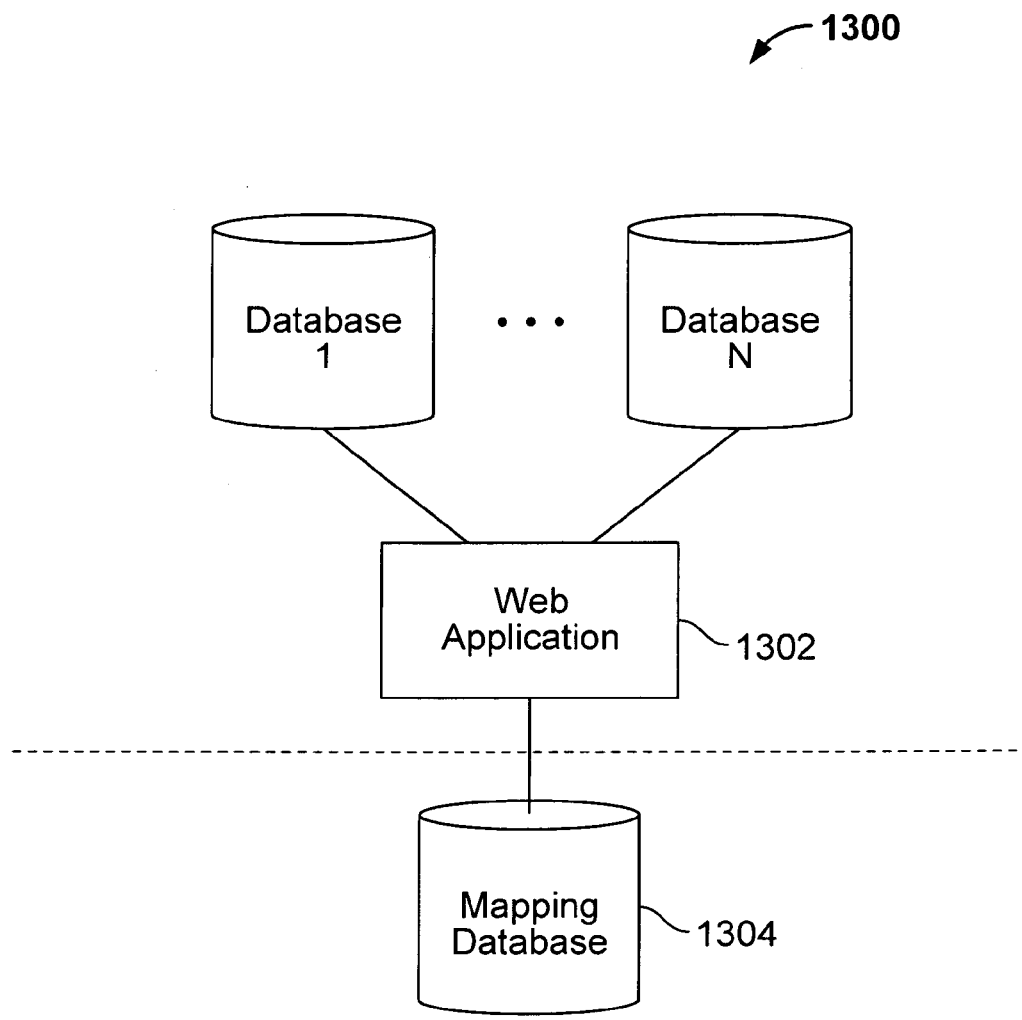
FIG. 13 is a block diagram illustrating an embodiment of a system for separating different types of data.

FIG. 13 is a block diagram illustrating an embodiment of a system for separating different types of data. In some cases, it would be undesirable to link the different types of data to each other. For example, a first type of data might include names and a second type of data might include social security numbers, and it might be undesirable to link the names and social security numbers in a banking database. As such, the names might be located in a first database and the social security numbers might be located in a second database. In this example, the system separates identifying data from personal data. In the example shown, system 1300 is shown to include N databases (database 1 to database N), web application 1302, and mapping database 1304. Database 1 comprises a plurality of identifying records containing identifying data. In some embodiments, the identifying records are profile records. Each of databases 2-N comprises a plurality of personal records containing personal data. In some embodiments, database 2 contains genotype records and database 3 contains phenotype records. Web application 1302 is an Internet application that provides personal data, such as genetic data, to users and allows users to share their personal data if desired. Web application 1302 obtains data from records in one or more of the N databases as needed and provides the data in web pages.

Mapping database 1304 is used to map records between databases. For example, each record in mapping database 1304 includes a mapping from database 1 to database 2 . . . to database N. Mapping database 1304 is used to determine which records belong to which individuals. In other words, mapping database 1304 is used to determine which personal records belong to an identifying record.

In some embodiments, mapping database 1304 is logically separate from the N databases and web application 1302. In some embodiments, database 1304 is also physically separated. By logically separating database 1304 from the N databases and web application 1302, if a hacker were able to gain access to data in any of the N databases, the hacker would not also be able to determine which personal records belong to which identifying record.

In some embodiments, mapping database 1304 is in a more secure and protected environment than web application 1302 or databases 1-N. For example, web application 1302 may have vulnerabilities because it has numerous pages (that are constantly evolving with new features), each of which could have a programming error that provides a security hole. Mapping database 1304 could have just one port open and only accept and/or respond to a limited set of requests. Mapping database 1304 could be on a separate physical server located at a highly secure offsite location.

Figure 14:
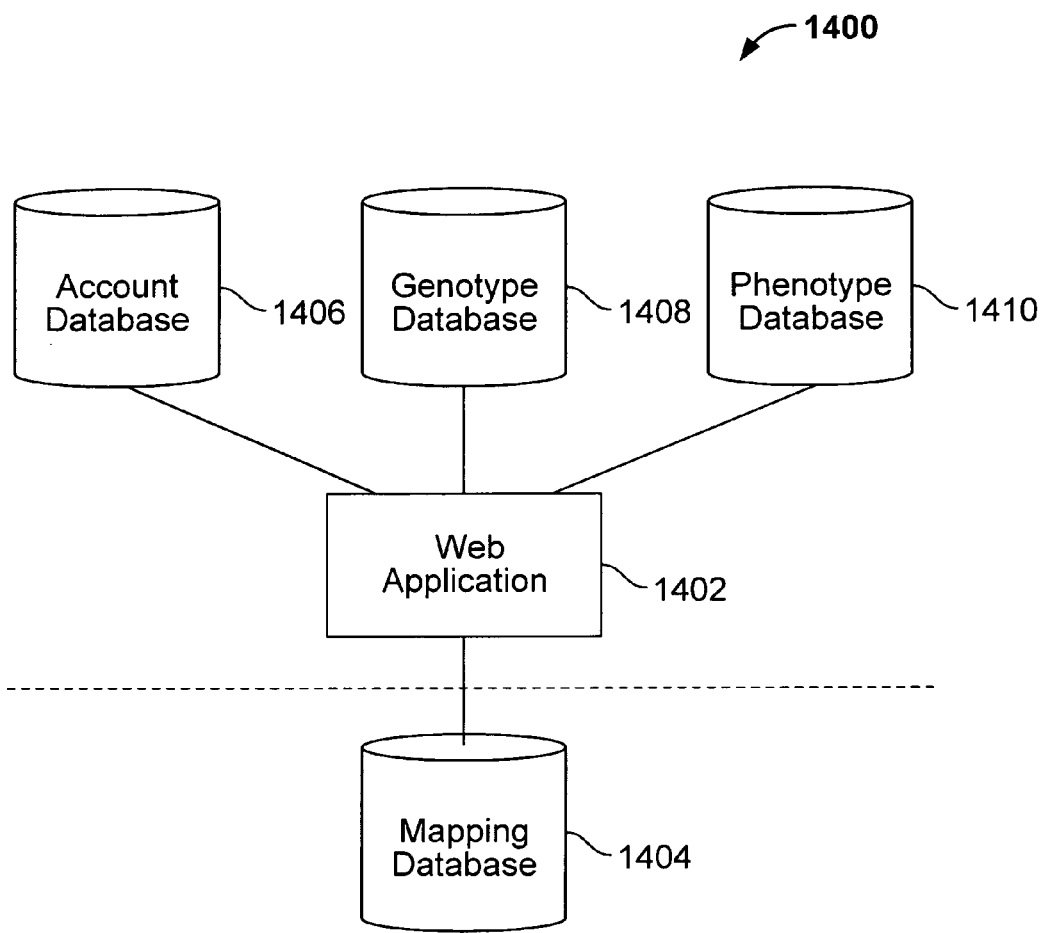
FIG. 14 is a block diagram illustrating an embodiment of a system for separating identifying account data from genotype data and phenotype data.

FIG. 14 is a block diagram illustrating an embodiment of a system for separating identifying account data from genotype data and phenotype data. System 1400 is an embodiment of system 1300 in which N=3. Account database 1406 contains profile records, such as profile records 1102. Genotype database 1408 contains genotype records, such as genotype records 1106. Phenotype database 1410 contains phenotype records, such as phenotype records 1104. Web application 1402 accesses account database 1406, genotype database 1408, and phenotype database 1410, as needed. Web application 1402 determines which phenotype and genotypes records map to which account or profile using mapping database 1404. In some embodiments, mapping database 1404 is logically separate from web application 1402, account database 1406, genotype database 1408, and phenotype database 1410. Mapping database 1404 includes a plurality of mapping records.

FIG. 15 is a diagram illustrating an embodiment of mapping records in a mapping database. In the example shown, mapping records 1500 are stored in a mapping database, such as mapping database 1404. Each mapping record (row) shows which genotype record and phenotype record belongs to each profile record based on the identifiers of each record. Thus, profile ID 10001 maps to genotype ID 30004 and phenotype ID 20003. Referring to FIG. 11B, this means that John Doe is 5'10", weighs 170 lbs, has brown eyes, brown hair, SNP data SNP_y, Test Result 1 of yes, and Test Result 2 of 1.1. For example, SNP_y may include the calls for a plurality of SNPs. Test Result 1 may be whether the individual perceives the bitter taste in broccoli. Test Result 2 may be risk for type 1 diabetes; 0.14 out of 100 people with the individual's genotype and ethnicity will get type 1 diabetes between the ages of 0 and 19.

Referring to FIG. 11A, in some embodiments, some of the fields shown in profile records 1102 are stored in separate records in a separate database. For example, the "Birthdate", "Birthplace", and "Ancestry" fields might be stored in biographical records in a biographical database. The biographical records might also include a social security number. Mapping records 1500 would also include a column for biographical ID to indicate an additional mapping to a biographical record having a biographical ID. This way, should a hacker obtain access to only the profile records, he would not be able to determine which profile records (which contain the names of the individuals) belong to which biographical records (which contains the birthdate of the individuals). This may be useful to address concerns about identity theft.

Other examples of system 1300 include a banking system. For example, there may be a database of names, a database of birthdates, and a database of social security numbers. Mapping database 1304 maps names to birthdates and social security numbers. In other words, each mapping record might include a name record ID, a birthdate record ID, and a social security number record ID. Thus, a hacker who obtains access to a name record would not know which birthdate or social security number goes with that name, and is less likely to be able to compromise that individual's identity. By separating identifying data from personal data (e.g., genotype and/or phenotype data), system 1300 can be called a "de-identification" system that "de-identifies" the personal data from the identifying data.

Figure 16:
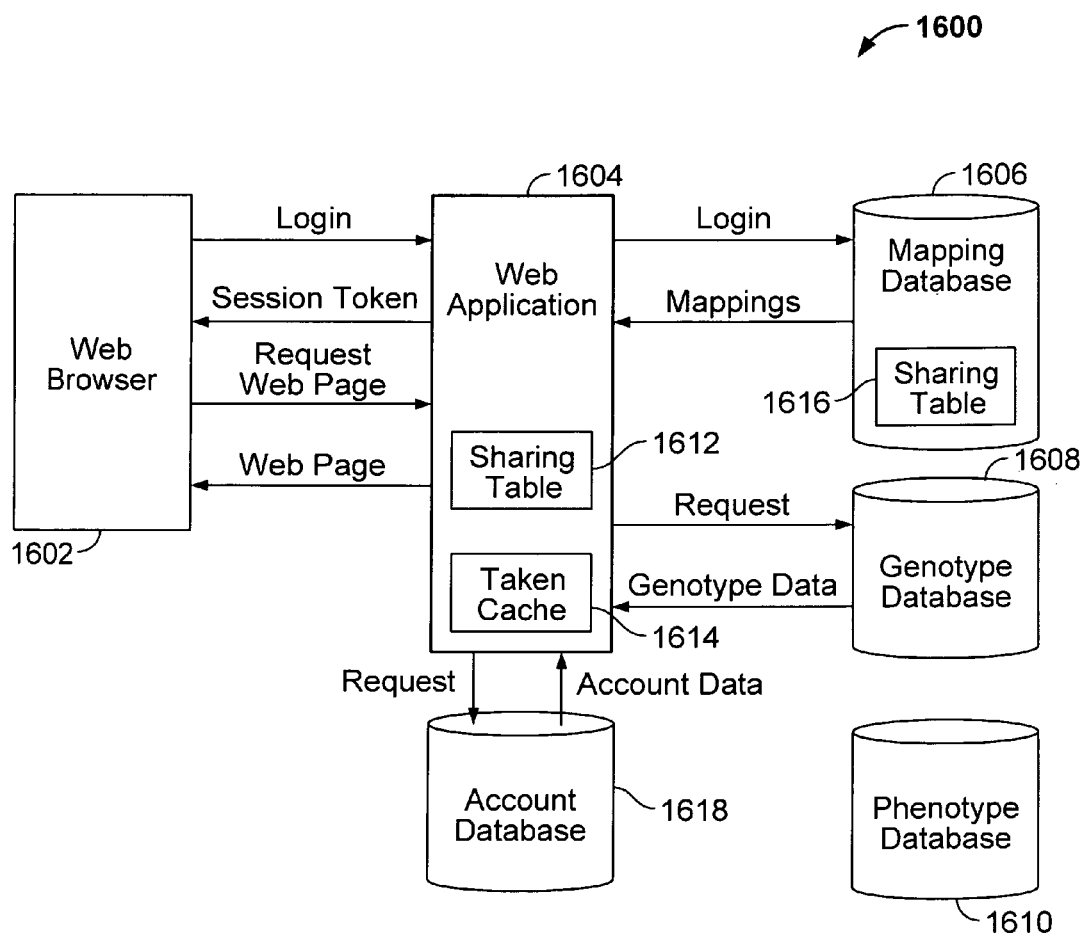
FIG. 16 is a block diagram illustrating an embodiment of a system for separating identifying account data from genotype data and phenotype data.

FIG. 16 is a block diagram illustrating an embodiment of a system for separating identifying account data from genotype data and phenotype data. System 1600 is shown to include web browser 1602, web application 1604, account database 1618, phenotype database 1610, genotype database 1608, and mapping database 1606. In some embodiments, web browser 1602 is running on a user's computer and web application 1604 is running on a web server. Web application 1604, account database 1618, phenotype database 1610, genotype database 1608, and mapping database 1606 are examples of web application 1402, account database 1406, phenotype database 1410, genotype database 1408, and mapping database 1404, respectively. In some embodiments, mapping database 1606 contains or has access to sharing table 1616 and/or web application 1614 contains or has access to sharing table 1612. Sharing table 1611 and sharing table 1616 are identical and an appropriate replication mechanism is used to maintain consistency of the data between the tables. For example, in some embodiments, updates are first made to sharing table 1616 before they can be propagated to sharing table 1612.

In the example shown, a user of web browser 1602 logs into web application 1604. For example, the user (e.g., Bob Lee) logs into an account by providing a username (e.g., boblee) and password. The username and password are received by web application 1604, which validates the login and then forwards the username and password to mapping database 1606. Mapping database 1606 consults sharing table 1616 to determine which profiles are shared to boblee's account. Mapping database 1606 obtains a set of mappings, including mapping(s) for the profile(s) in boblee's account and mapping(s) for the profiles that are shared to boblee's account. Mapping database 1606 returns the set of mappings to web application 1604.

FIG. 17 is a diagram illustrating a set of mappings for boblee. In the example shown, mappings 1700 includes mapping(s) for the profile(s) in boblee's account and mapping(s) for the profiles that are shared to boblee's account based on a sharing table, such as sharing table 1200. As shown, the profile record to genotype record to phenotype record mapping is shown for profile ID 10003 (Bob Lee), 10001 (John Doe), and 10002 (Mary Doe). Mappings for John Doe and Mary Doe are also provided because John Doe's profile and Mary Doe's profile are shared to account boblee, as shown in sharing table 1200. In some embodiments, mappings 1700 also include sharing level and/or other information.

Returning to FIG. 16, the set of mappings are received by web application 1604. The mappings are stored along with a session token in a token cache 1614. FIG. 18 is a diagram illustrating an embodiment of a token cache. Token cache 1800 is an example of token cache 1614. As shown, each entry or record in token cache 1800 includes a "Session Token", a "Mapping", and a "Sharing Level". The "Session Token" is a number that is uniquely associated with the entry and may be generated by web application 1604 or mapping database 1606. "Mapping" includes the set of mappings for the profile in boblee's account and for the profiles that are shared to boblee's account. "Sharing Level" indicates the sharing level for each mapping. In some embodiments, there is no sharing level indicated for mapping 10003 to 20005 to 30001 because that mapping is Bob Lee's mapping and a user of boblee's account has access to all of the data in boblee's account.

Returning to FIG. 16, the session token is returned to web browser 1602. Web browser 1602 stores the session token for the duration of the session (e.g., until the user logs out or the session times out). In some embodiments, the session token is stored in a cookie. The login process is now complete and the session is initiated.

Web browser 1602 then requests a web page. For example, Bob Lee uses web browser 1602 to request a web page that displays Test Result 1, e.g., whether individuals can perceive the bitter taste in broccoli. The web page request, including the token, is sent to web application 1604. Web application 1604 validates the token and then looks up the token in the token cache to obtain the mappings associated with the account (e.g., boblee). Now that web application 1604 has the mappings, it can obtain Test Result 1 for each of the profiles visible to account boblee, provided that Test Result 1 is included in the Sharing Level for the sharing relationship. In some embodiments, web application 1604 retrieves names associated with each profile from account database 1618. Web application 1604 retrieves the genotype record for each profile from genotype database 1608. In some embodiments, only Test Result 1 for each profile is obtained from genotype database 1608. Web application 1604 then provides the names and Test Result 1 next to each name in a web page. The web page is displayed in web browser 1602.

FIG. 19 is a diagram illustrating an embodiment of profile records in a system with publishing and group sharing features. In the example shown, profile records 1900 shows profile records 1102 with two additional columns or fields: "Public Data" and "Group Data".

In some embodiments, a user may decide to publish a profile or a subset of data in a profile to the public. As used herein, publishing to or sharing with or to the public means sharing with all users. The data published to the public is referred to as public data. In some embodiments, the public data is copied to a profile record. This means that a mapping from a mapping database is no longer needed in order to access the user's name and public data. For example, if a user of account familydoe decides to publish to the public Test Result 1 for profile John Doe, the data for Test Result 1 is copied to profile 10001 (which corresponds to John Doe). In some embodiments, the data for Test Result 1 is included in the "Public Data" field in the profile record. Now, web application 1604 just needs to access John Doe's profile record in order to obtain Test Result 1. This eliminates the need to provide the mapping for John Doe's profile to every account. In addition, by not having to provide the mapping for John Doe's profile to every account, efficiency is improved.

In some embodiments, a user may decide to publish a profile or a subset of data in a profile to a group. As used herein, publishing to or sharing with or to a group means sharing to all members (accounts that are members) of a group. The data published to a group is referred to as group data. In some embodiments, group data is copied to the "Group Data" field in the profile record. For example, as shown in FIG. 19, a user of account familydoe has published John Doe's weight to group 60002. For example, there may be a table of groups and each group has a group ID and a list of member accounts. This eliminates the need to provide the mapping for John Doe's profile to every account in the group, which may pose security risks. In addition, efficiency is improved.

Figure 20:
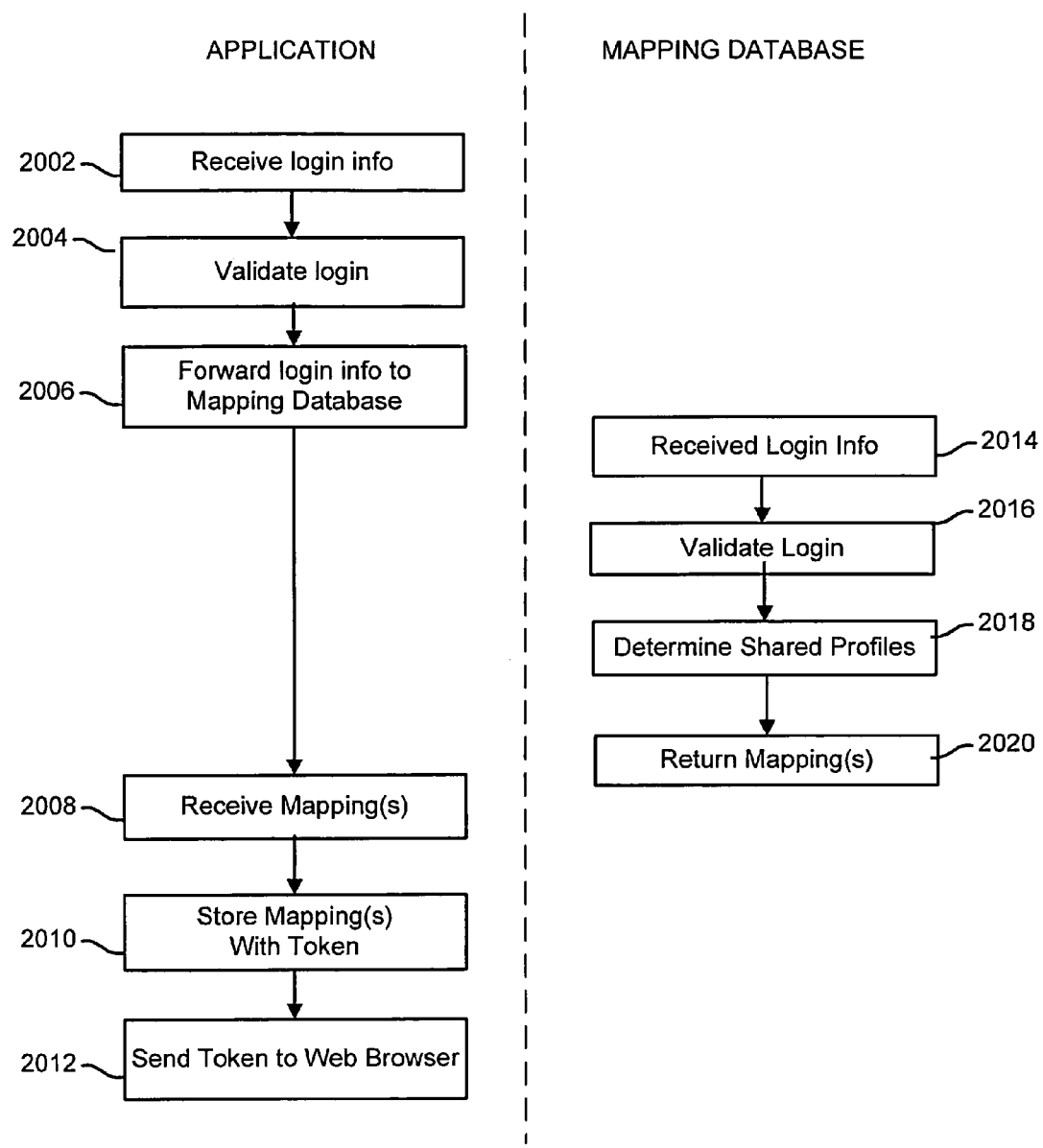
FIG. 20 is a flow chart illustrating an embodiment of processes in a system for separating identifying account data from genotype data and phenotype data.

FIG. 20 is a flow chart illustrating an embodiment of processes in a system for separating identifying account data from genotype data and phenotype data. In some embodiments, steps 2002-2012 are performed by web application 1604 and steps 2014-2020 are performed by mapping database 1606.

In the example shown, at 2002, login information is received. For example, a username and password are received from a web browser, such as web browser 1602. At 2004, the login information is validated. For example, it is determined whether the username exists, and then the password is encrypted and compared with a stored version of the encrypted password to determine validity. If the login information is validated, then at 2006, the login information (e.g., the username and password) is forwarded to a mapping database.

At 2014, the login information is received by the mapping database. At 2016, the login information is validated. For example, it is determined whether the username exists, and then the password is encrypted and compared with a stored version of the encrypted password to determine validity. If the login information is validated, then at 2018, shared profiles are determined. In some embodiments, a sharing table, such as sharing table 1616 or 1200, is consulted to determine which profiles are to be shared with the account associated with the username. At 2020, mappings associated with the profiles are returned to the web application. In some embodiments, the mappings are similar to mappings 1700. In some embodiments, the mappings include sharing level information.

At 2008, the mappings are received by the web application. At 2010, the mappings are stored in a token cache with a token. For example, the mappings are stored in token cache 1614 or 1800 with a token generated by mapping database 1606. In various embodiments, the token may be generated in various ways. In some embodiments, the token is generated based on the mappings. For example, the token may comprise the mappings appended to each other or the token may comprise a hash of the mappings appended to each other. The token is stored with the mappings. In some embodiments, the token is stored as an encrypted token, where the encryption changes from session to session. The token could be encrypted by the web application or by the mapping database in various embodiments. In some embodiments, sharing level information is also stored in the token cache. At 2012, the token is sent to a web browser, such as web browser 1602. In some embodiments, the token is stored as a cookie.

A token is an example of mapping data associated with a mapping. In various embodiments, any appropriate mapping data associated with a mapping may be used (e.g., sent to the web browser and received from the web browser, as more fully described below). Mapping data associated with a mapping could include a mapping identifier or a mapping indicator, such as a lookup key, a token, or the mapping itself. In the case of the mapping itself, rather than sending a token, data representative of the mapping may be sent, such as the mappings appended to each other, as previously described. Mapping data associated with the mapping may be generated by a web application and/or a mapping database.

Figure 21:
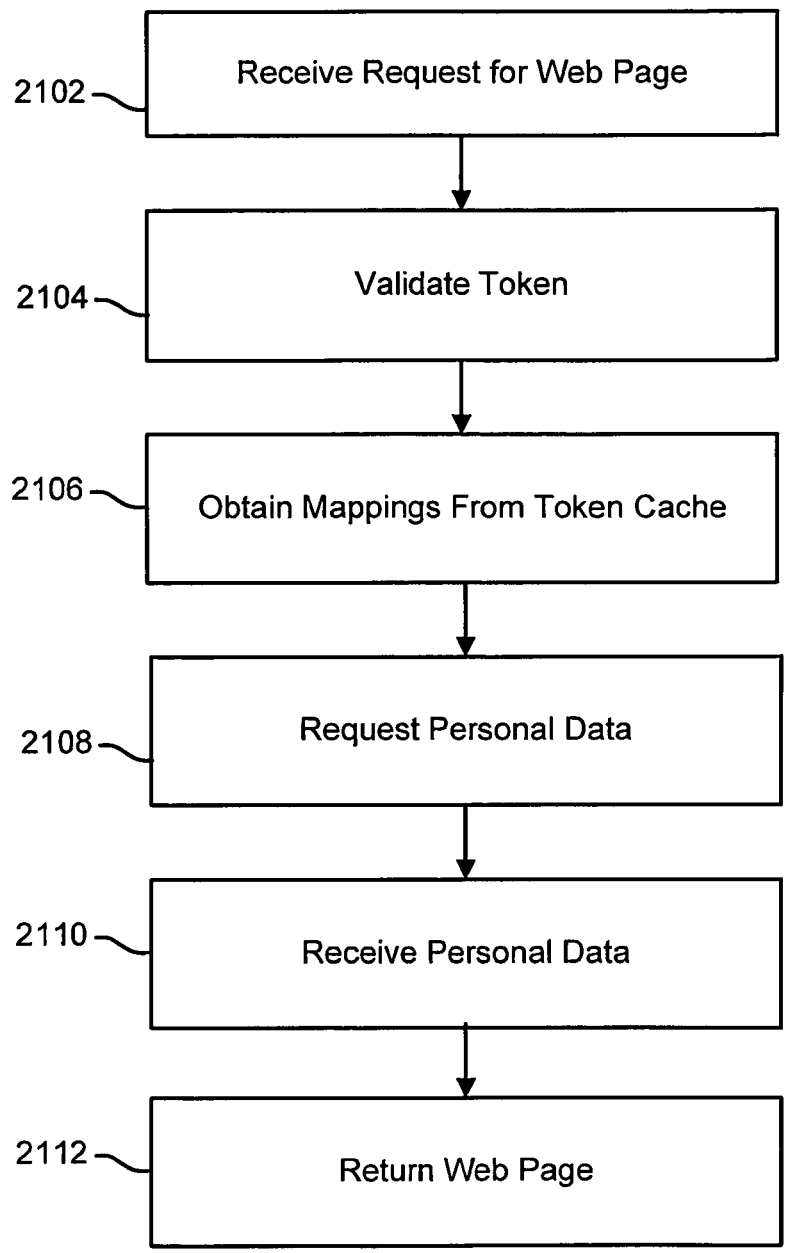
FIG. 21 is a flow chart illustrating an embodiment of processing a request for a web page.

FIG. 21 is a flow chart illustrating an embodiment of processing a request for a web page. In some embodiments, each time there is a request for a web page, this process is performed by web application 1604. In the example shown, at 2102, a request for a web page is received. For example, a user uses a web browser to select a link to a web page that shows whether individuals can perceive the bitter taste in broccoli. In some embodiments, the request includes the token that was provided to the web browser at 2012. In some embodiments, the token is passed to the web application separately. At 2104, the token is validated. For example, it is determined if the token has timed out, and if not, the token is encrypted and compared with a stored version of the encrypted token to determine validity. At 2106, using the token, mapping(s) are obtained from the token cache. In some embodiments, the mapping(s) were stored in the token cache at 2010. In some embodiments, sharing levels are obtained from a sharing table, such as sharing table 1612. In some embodiments, sharing levels were stored in the token cache at 2010. At 2108, personal data is requested. For example, if the mappings look like mapping 1700, genotype records for genotype ID 30001, 30004, and 30003 are requested from a genotype database, such as genotype database 1608. At 2110, personal data is received. For example, genotype records for genotype ID 30001, 30004, and 30003 are received from a genotype database. At 2112, the web page is returned. For example, data related to whether individuals can perceive the bitter taste in broccoli is retrieved from the genotype records for genotype ID 30001, 30004, and 30003 and included in the web page. In some embodiments, data is included in the web page only if the data is permitted to be shared based on the sharing level associated with the data.

Figure 22:
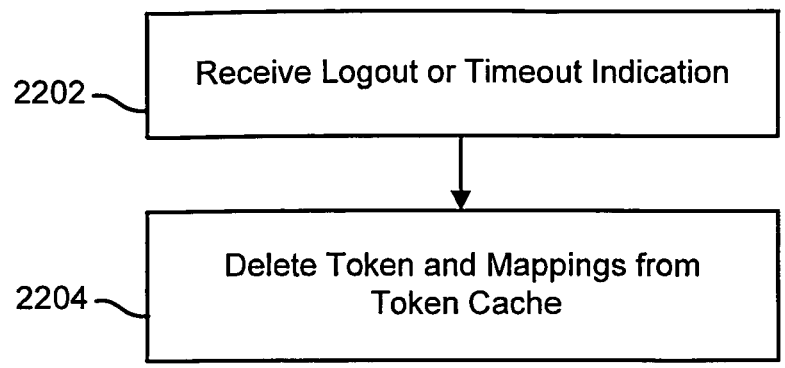
FIG. 22 is a flow chart illustrating an embodiment of a process for terminating a session.

FIG. 22 is a flow chart illustrating an embodiment of a process for terminating a session. In some embodiments, this process is performed by web application 1604. At 2202, a logout or time out indication is received. For example, the user of web browser 1602 has logged out or has not been active for a particular length of time. At 2204, the token and mappings associated with the account are deleted from the token cache. The session is now terminated. Thus, the user needs to login again in order to obtain a new token and be able to request web pages with personal data.

Figure 23:
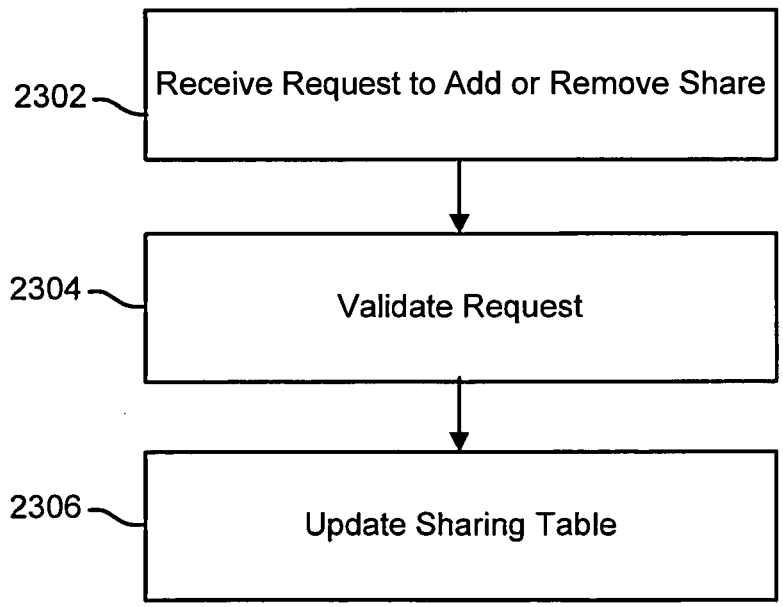
FIG. 23 is a flow chart illustrating an embodiment of a process for updating sharing information in a mapping database.

FIG. 23 is a flow chart illustrating an embodiment of a process for updating sharing information in a mapping database. In some embodiments, this process is performed by mapping database 1606. At 2302, a request to update sharing information is received. Examples of updates to sharing information include: adding a profile to be shared to an account, removing a profile from being shared to an account, updating sharing level information for a particular profile being shared to an account. At 2304, the request is validated. For example, in order to process the request, a username and password associated with the profile must be received. In some embodiments, upon receipt of the username and password, it is determined whether the username exists, and then the password is encrypted and compared with a stored version of the encrypted password to determine validity. At 2306, the sharing table is updated. For example, in sharing table 1200, a record may be added or deleted, or one of the sharing levels may be modified. In some embodiments, the update is propagated to other copy(ies) of the sharing table, such as sharing table 1612.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for separating identifying data from personal data, comprising:
   one or more computer data storages that store:
      a first set of stored data stored in a computer data storage comprising a plurality of identifying data structures containing identifying data, wherein each identifying data structure is associated with a different individual;
      a second set of stored data stored in a computer data storage comprising a plurality of personal data structures containing personal data, wherein the personal data includes genetic data comprising genome data, single nucleotide polymorphism (SNP) data, or a combination thereof;
      a plurality of accounts, wherein each account is associated with at least one identifying data structure; and
      a set of mapping data stored in a secure mapping computer data storage and comprising a plurality of mappings, wherein:
         (1) each mapping is between an identifying data structure and a personal data structure; and
         (2) the secure mapping computer data storage is implemented in a more secure environment than that of either the identifying data or the genetic data; and
   one or more processors, coupled to the one or more computer data storages, that execute an application that:

receives, from a web browser, login information associated with an account;

validates the login information;

forwards the login information to the secure mapping computer data storage;

in response to forwarding the login information to the secure mapping computer data storage, receives, from the secure mapping computer data storage:

(1) a mapping from the identifying data to the genetic data for an individual associated with the account; and (2) for each individual profile being shared to the account, a mapping from the identifying data to the genetic data for that individual profile;

wherein the set of mapping data is in a logically separate database from the first set of stored data, the second set of stored data, and the application;

wherein the second set of stored data comprising the personal data structures does not contain identifying data used to identify an individual and in the event that an unauthorized user obtains access to the first set of stored data and the second set of stored data, the unauthorized user would not be able to determine which personal record is associated with each identifying record without access to the secure mapping computer data storage; and wherein a portion of a personal data structure is shared between more than one account, the portion of the personal data structure including less data than the personal data structure.

2. The system as recited in claim 1, wherein the first set of stored data comprises a database and the identifying data structures comprise database records.

3. The system as recited in claim 1, wherein the set of mapping data comprises a mapping database.

4. The system as recited in claim 1, wherein the application comprises a web application.

5. The system as recited in claim 1, wherein the mapping data comprises a token.

6. The system as recited in claim 5, wherein the application receives the token from a web browser.

7. The system as recited in claim 1, wherein the identifying data includes a name, a birth date, or a birth place.

8. The system as recited in claim 5, wherein the token is encrypted.

9. The system as recited in claim 1, wherein the token is associated with multiple mappings.

10. The system as recited in claim 9, wherein the multiple mappings are based at least in part on sharing information.

11. The system as recited in claim 5, wherein the token is stored as a cookie by a web browser.

12. The system as recited in claim 1, wherein the application determines multiple mappings and obtain multiple personal data structures based on the multiple mappings.

13. The system as recited in claim 1, wherein the identifying data structures include public data.

14. The system as recited in claim 1, wherein the identifying data structures include group data.

15. The system as recited in claim 1, wherein the token is deleted when a session terminates.

16. The system as recited in claim 1, further including a token cache that stores a plurality of tokens and one or more mappings for each token.

17. The system as recited in claim 1, further including sharing information that indicates which personal data structures are shared to an account.

18. A computer implemented method for sharing data, comprising:

receiving, at a web application, login information associated with an account;

validating the login information;

forwarding the login information to a secure mapping computer data storage containing a set of mapping data comprising a plurality of mappings, wherein:

(1) each mapping is between an identifying data structure and a personal data structure; and (2) the secure mapping computer data storage is implemented in a more secure environment than that of either identifying data or genetic data;

in response to forwarding the login information to the secure mapping computer data storage, receiving, from the secure mapping computer data storage:

(1) a mapping from the identifying data to the genetic data for an individual associated with the account; and (2) for each individual profile being shared to the account, a mapping from the identifying data to the genetic data for that individual profile;

storing the received mappings; and sending mapping data associated with the received mappings to a web browser;

wherein the set of mapping data is in a logically separate database from a first set of stored data comprising a plurality of identifying data structures containing the identifying data and a second set of stored data comprising a plurality of personal data structures containing the personal data, the personal data including genetic data comprising genome data, single nucleotide polymorphism (SNP) data, or a combination thereof;

wherein the second set of stored data comprising the personal data structures does not contain identifying data used to identify an individual and in the event that an unauthorized user obtains access to the first set of stored data and the second set of stored data, the unauthorized user would not be able to determine which personal record is associated with each identifying record without access to the secure mapping computer data storage; and wherein a portion of a personal data structure is shared between more than one account, the portion of the personal data structure including less data than the personal data structure.

19. The method as recited in claim 18, wherein storing includes storing the one or more mappings with a token.

20. The method as recited in claim 18, wherein the mapping data comprises a token.

21. The method as recited in claim 18, wherein the mapping data comprises the one or more mappings.

22. The method as recited in claim 18, wherein each mapping maps an identifying data structure containing identifying data to a personal data structure containing personal data.

23. The method as recited in claim 18, wherein the set of one or more mappings includes a mapping for each individual whose personal data is shared to the account.

24. The method as recited in claim 20, further including:

receiving a request for a web page containing personal data;

receiving the token;

validating the token;

obtaining the one or more mappings based at least in part on the token;

requesting the personal data based on the one or more mappings;

receiving the personal data; and returning the web page.

25. A method for sharing data, comprising:
receiving, at a secure mapping computer data storage, login information associated with an account, wherein the secure mapping computer data storage stores a set of mapping data comprising a plurality of mappings, wherein:
(1) each mapping is between an identifying data structure and a personal data structure; and
(2) the secure mapping computer data storage is implemented in a more secure environment than that of either the identifying data or the genetic data;
validating the login information;
in response to receiving the login information at the secure mapping computer data storage, determining:
(1) a mapping from the identifying data to the genetic data for an individual associated with the account; and
(2) for each individual profile being shared to the account, a mapping from the identifying data to the genetic data for that individual profile;
returning the determined mappings;
wherein the secure mapping computer data storage contains a set of one or more mappings and are in a logically separate database from a first set of stored data comprising a plurality of identifying data structures containing the identifying data and the second set of stored data comprising a plurality of personal data structures containing the personal data, the personal data including genetic data comprising genome data, single nucleotide polymorphism (SNP) data, or a combination thereof;
wherein the second set of stored data comprising the personal data structures does not contain identifying data used to identify an individual and in the event that an unauthorized user obtains access to the first set of stored data and the second set of stored data, the unauthorized user would not be able to determine which personal record is associated with each identifying record without access to the secure mapping computer data storage; and
wherein a portion of a personal data structure is shared between more than one account, the portion of the personal data structure including less data than the personal data structure.

26. The method as recited in claim 25, wherein determining includes consulting sharing information.

27. The method as recited in claim 25, further including generating a token and returning the token with the mappings.

28. The method as recited in claim 25, further including storing sharing information.

29. The system as recited in claim 1, wherein the sharing is unidirectional.

* * * * *